United States Patent [19]
Gryskiewicz et al.

[11] Patent Number: 5,935,118
[45] Date of Patent: *Aug. 10, 1999

[54] ABSORBENT ARTICLE INCLUDING LIQUID CONTAINMENT BEAMS

[75] Inventors: Stanley Michael Gryskiewicz, Woodstock; Frank Jerrel Akin, Marietta; David Martin Jackson, Roswell, all of Ga.; Earle Harry Sherrod, Appleton, Wis.

[73] Assignee: Kimberly-Clark Worldwide, Inc., Neenah, Wis.

[ * ] Notice: This patent is subject to a terminal disclaimer.

[21] Appl. No.: 08/986,660

[22] Filed: Dec. 8, 1997

Related U.S. Application Data

[63] Continuation of application No. 08/473,055, Jun. 7, 1995, abandoned.

[51] Int. Cl.⁶ .................................................. A61F 13/15
[52] U.S. Cl. ..................................... 604/385.1; 604/385.2
[58] Field of Search ............................ 604/385.1, 385.2, 604/378, 395

[56] References Cited

U.S. PATENT DOCUMENTS

| | | |
|---|---|---|
| Re. 33,351 | 9/1990 | Papajohn . |
| 75,036 | 3/1868 | Manheim . |
| 709,223 | 9/1902 | James et al. . |
| 810,128 | 1/1906 | Green . |
| 810,130 | 1/1906 | Green . |
| 810,133 | 1/1906 | Green . |
| 2,069,092 | 1/1937 | Jackson, Jr. ............... 128/284 |
| 2,331,271 | 10/1943 | Gilchrist ..................... 128/284 |
| 3,081,772 | 3/1963 | Brooks et al. .............. 128/287 |
| 3,364,931 | 1/1968 | Hirsch ....................... 128/290 |
| 3,572,342 | 3/1971 | Lindquist et al. .......... 128/287 |
| 3,612,055 | 10/1971 | Mesek et al. ............... 128/287 |
| 3,699,966 | 10/1972 | Chapuis ................. 128/290 R |
| 3,768,480 | 10/1973 | Mesek et al. ............... 128/287 |

(List continued on next page.)

FOREIGN PATENT DOCUMENTS

| | | |
|---|---|---|
| 0 130 848 A2 | 1/1985 | European Pat. Off. ........ A61F 13/18 |
| 0 219 326 A2 | 4/1987 | European Pat. Off. ........ A41B 13/02 |
| 0337969A1 | 10/1989 | European Pat. Off. . |
| 0422504A2 | 4/1991 | European Pat. Off. . |
| 0 491 390 A1 | 12/1992 | European Pat. Off. ........ A61F 13/15 |
| 0687453A1 | 12/1995 | European Pat. Off. . |
| 2-152450 | 6/1990 | Japan ................. A61F 5/44 |
| 2100130 | 12/1982 | United Kingdom . |
| 2209672 | 5/1989 | United Kingdom . |
| 2 251 172 | 1/1992 | United Kingdom ............ A61F 13/15 |
| 2 251 172 | 7/1992 | United Kingdom ............ A61F 13/15 |
| 2263622 | 8/1993 | United Kingdom . |
| 2263914 | 8/1993 | United Kingdom . |
| 22/70247 | 3/1994 | United Kingdom . |
| 2 284 550 | 6/1995 | United Kingdom ............ A61F 13/15 |
| WO89/09549 | 10/1989 | WIPO . |
| WO 93/10733 | 6/1993 | WIPO ............... A61F 13/15 |
| WO93/12746 | 7/1993 | WIPO . |
| WO93/14729 | 8/1993 | WIPO . |
| WO 96/40029 A1 | 12/1996 | WIPO ............... A61F 13/15 |

OTHER PUBLICATIONS

American Society for Testing Materials (ASTM) Designation: E 96–80, "Standard Test Methods for Water Vapor Transmission of Materials," pp. 777–785, published Feb. 1981.

*Primary Examiner*—Bruce Snow
*Attorney, Agent, or Firm*—Patricia A. Charlier

[57] ABSTRACT

An absorbent article includes a garment shell and at least one liquid containment beam formed of an absorbent material. The liquid containment beam has an attachment edge bonded to the garment shell so that the containment beam can lie against the garment shell and also pivot about an axis defined by the attachment edge. For comfort during use, the containment beam desirably has a width to thickness ratio of at least about 3:1. In particular embodiments, the absorbent article includes pairs of inner and outer containment beams, with the inner containment beams adapted to lie against the garment shell and the outer containment beams adapted to lie against the inner containment beams.

9 Claims, 8 Drawing Sheets

U.S. PATENT DOCUMENTS

| | | | |
|---|---|---|---|
| 3,863,637 | 2/1975 | MacDonald et al. | 128/287 |
| 3,954,107 | 5/1976 | Chesky et al. | 128/290 R |
| 4,029,101 | 6/1977 | Chesky et al. | 128/290 R |
| 4,100,324 | 7/1978 | Anderson et al. | 428/288 |
| 4,230,113 | 10/1980 | Mehta | 128/287 |
| 4,388,075 | 6/1983 | Mesek et al. | 604/385 |
| 4,413,996 | 11/1983 | Taylor | 604/382 |
| 4,451,934 | 6/1984 | Gioello | 2/113 |
| 4,589,876 | 5/1986 | Van Tilburg | 604/385 R |
| 4,604,313 | 8/1986 | McFarland et al. | 428/172 |
| 4,610,679 | 9/1986 | Matsushita | 604/369 |
| 4,610,682 | 9/1986 | Kopp | 604/385 R |
| 4,657,539 | 4/1987 | Hasse | 604/385 A |
| 4,695,278 | 9/1987 | Lawson | 604/385 A |
| 4,699,823 | 10/1987 | Kellenberger et al. | 428/219 |
| 4,704,116 | 11/1987 | Enloe | 604/385 A |
| 4,713,069 | 12/1987 | Wang et al. | 604/378 |
| 4,753,644 | 6/1988 | Cottenden et al. | 604/378 |
| 4,753,645 | 6/1988 | Johnson | 604/378 |
| 4,756,726 | 7/1988 | Peace | 55/275 |
| 4,781,711 | 11/1988 | Houghton et al. | 604/378 |
| 4,787,896 | 11/1988 | Houghton et al. | 604/385.1 |
| 4,798,603 | 1/1989 | Meyer et al. | 604/378 |
| 4,840,692 | 6/1989 | Kamstrup-Larsen | 156/252 |
| 4,892,535 | 1/1990 | Bjornberg et al. | 604/380 |
| 4,909,803 | 3/1990 | Aziz et al. | 604/385.2 |
| 4,935,021 | 6/1990 | Huffman et al. | 604/385.1 |
| 4,938,754 | 7/1990 | Mesek | 604/385.2 |
| 4,940,464 | 7/1990 | Van Gompel et al. | 604/396 |
| 4,988,344 | 1/1991 | Reising et al. | 604/368 |
| 5,066,527 | 11/1991 | Newell | 428/35.6 |
| 5,133,371 | 7/1992 | Sivess | 132/212 |
| 5,147,343 | 9/1992 | Kellenberger | 604/368 |
| 5,151,091 | 9/1992 | Glaug et al. | 604/385.1 |
| 5,167,653 | 12/1992 | Igaue et al. | 604/385.2 |
| 5,176,672 | 1/1993 | Bruemmer et al. | 604/385.1 |
| 5,192,606 | 3/1993 | Proxmire et al. | 428/284 |
| 5,207,662 | 5/1993 | James | 604/385.2 |
| 5,207,664 | 5/1993 | Blanco | 604/385.2 |
| 5,211,641 | 5/1993 | Roos et al. | 604/385.1 |
| 5,227,107 | 7/1993 | Dickenson et al. | 264/113 |
| 5,304,159 | 4/1994 | Tanji et al. | 604/385.2 |
| 5,350,624 | 9/1994 | Georger et al. | 428/219 |
| 5,364,382 | 11/1994 | Latimer et al. | 604/378 |
| 5,366,453 | 11/1994 | Zehner et al. | 604/385.2 |
| 5,382,246 | 1/1995 | Kawano | 604/385.2 |
| 5,386,595 | 2/1995 | Kuen et al. | 2/400 |
| 5,399,175 | 3/1995 | Glaug et al. | 604/385.1 |
| 5,464,402 | 11/1995 | Zajaczkowski | 604/385.1 |
| 5,486,166 | 1/1996 | Bishop et al. | 604/366 |
| 5,490,846 | 2/1996 | Ellis et al. | 604/366 |
| 5,490,847 | 2/1996 | Correa et al. | 604/387 |
| 5,509,915 | 4/1996 | Hanson et al. | 604/378 |
| 5,575,785 | 11/1996 | Gryskiawicz et al. | 604/385.2 |
| B1 4,315,508 | 11/1988 | Bolick | 604/392 |

ABSORBENT ARTICLE INCLUDING LIQUID CONTAINMENT BEAMS

"This is a continuation application of application U.S. Ser. No. 08/473,055, filed on Jun. 7, 1995 now abandoned."

BACKGROUND OF THE INVENTION

The present invention relates to articles for absorbing body fluids. More particularly, the invention pertains to an absorbent article including one or more containment beams that absorb liquid and impede liquid flow.

Disposable absorbent articles such as incontinence undergarments, diapers, feminine products, or the like have commonly included a liquid permeable bodyside liner, a liquid impermeable moisture barrier, and a generally flat absorbent material disposed between the bodyside liner and the moisture barrier. A substantial portion of the absorbent material is routinely positioned in the crotch region of the article where it is likely to directly receive insults of liquid. Because the absorbent material tends to swell upon taking in the first insult of liquid, however, the amount of void space in the crotch region available to receive subsequent insults is substantially reduced.

It has also been common for disposable absorbent articles to include elastic components, such as leg elastics, waist elastics, and/or elastic fastening devices. The function of these elastic components has been to improve the fit of the absorbent article about the wearer, and thereby enhance the containment of waste materials. Typically, however, the absorbent material is fully bonded or otherwise held immobile between the bodyside liner and the moisture barrier. Consequently, the impact of elastic components has been limited to sealing the periphery of the absorbent article against the body of the wearer, rather than controlling the shape of the article when it is worn.

Therefore, what is lacking and needed in the art is an absorbent article that maintains void space for multiple insults of liquid and that has an absorbent structure which promotes a product shape that enhances liquid containment.

SUMMARY OF THE INVENTION

In response to the discussed deficiencies in the prior art, a new absorbent article has been developed. The absorbent article readily assumes a bucket shape when worn to aid in collecting liquids. Additionally, the selection and arrangement of the components of the absorbent article provide sufficient void space in an acquisition zone of the article to accept and distribute multiple insults of liquid.

In one aspect, the present invention concerns an absorbent article having a garment shell including a moisture barrier and defining an interior surface. A liquid containment beam of the absorbent article is formed of an absorbent material and has longitudinal ends, opposite attachment and free edges which extend between the longitudinal ends, and opposite top and bottom surfaces. The ends define therebetween a length dimension, the attachment and free edges define therebetween a width dimension, and the top and bottom surfaces define therebetween a thickness dimension. A ratio of the width dimension to the thickness dimension is at least about 3:1. The bottom surface is adapted to lie against the interior surface, and the attachment edge is bonded to the interior surface, so that the liquid containment beam can pivot about an axis defined by the attachment edge.

This aspect of the invention provides an absorbent structure in the form of a containment beam that is moveable relative to the moisture barrier. In particular, the containment beam is free to pivot about an axis defined by its attachment edge in response to movements of the wearer or swelling of the absorbent material. The containment beam, for example, may swell upon absorbing liquid and thereafter form a physical barrier to inhibit liquid movement within the absorbent article.

In particular embodiments, the absorbent article includes first and second liquid containment beams which are positioned transversely outward of an acquisition zone of the garment shell. For purposes of the present invention, the acquisition zone is considered to be the central third of the garment shell in both the longitudinal and transverse directions. The absorbent article may be configured so that the acquisition zone has a saturated retention capacity of less than about 10 percent, and more desirably less than about 5 percent, of the total saturated retention capacity of the absorbent article, for improved performance. The acquisition zone may include an acquisition/distribution material positioned between the containment beams so that the bottom surface of each containment beam is adapted to lie against the acquisition/distribution material. In this way, the absorbent material of the article is uncoupled into distinct containment beams located transversely outward from the longitudinal and transverse center of the article. This facilitates formation of a bucket shape, in which the containment beams form the sidewalls of the bucket. The acquisition zone forms the center of the bucket and functions to maintain sufficient void space to accommodate multiple insults of liquid. Also in particular embodiments, the ratio of the width dimension to the thickness dimension is at least about 5:1.

In another aspect, the present invention concerns an absorbent article having a garment shell including a moisture barrier and defining an interior surface. The absorbent article also includes first and second inner liquid containment beams formed of an absorbent material and first and second outer liquid containment beams. Each of the inner and outer liquid containment beams has longitudinal ends, opposite attachment and free edges which extend between the longitudinal ends, and opposite top and bottom surfaces. The attachment edge of each of the inner and outer liquid containment beams is bonded to the interior surface, so that the bottom surface of each of the inner containment beams is adapted to lie against the interior surface and the bottom surface of each of the outer containment beams is adapted to lie against the top surface of one of the inner containment beams. Each of the liquid containment beams can pivot about an axis defined by its attachment edge.

This aspect of the invention results in improved comfort for the wearer. The pairs of inner and outer containment beams are distinct structures as opposed to a single, integral absorbent structure. Consequently, the inner and outer beams can move independently of one another and are less resistant to forces tending to shape the absorbent article. Further, the shingled arrangement of the containment beams provides a gradual increase and then decrease in the thickness of the absorbent article when viewed in the transverse direction from the center to each side edge. This is particularly desirable from a comfort standpoint when the wearer is in a sitting position. In particular embodiments, each of the containment beams may comprise a plurality of discrete absorbent structures which are themselves in a shingled arrangement to further improve comfort.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
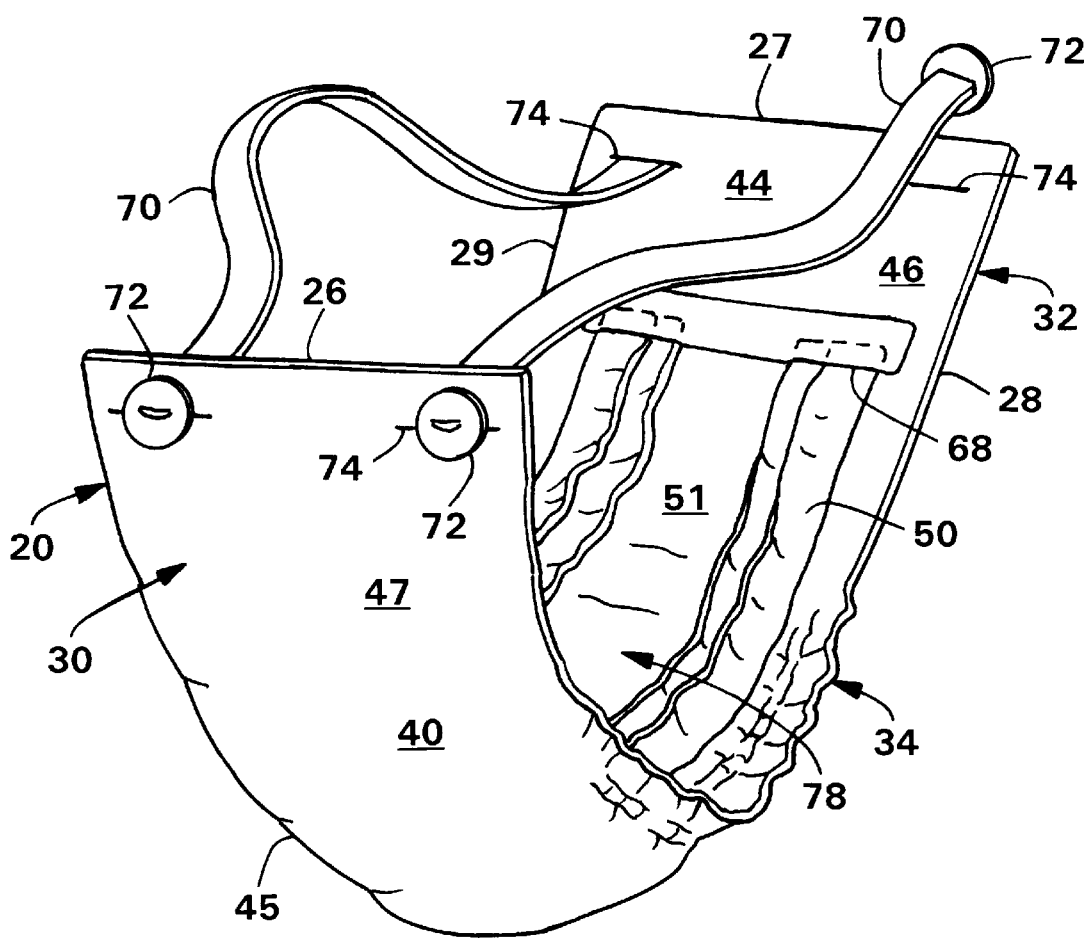
FIG. 1 representatively shows a perspective view of a disposable absorbent article according to the present invention.

Within the context of this specification, each term or phrase below will include the following meaning or meanings:

(a) "Bonded" refers to the Joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use and not intended to be washed and reused.

(c) "Disposed," "disposed on," "disposed with," "disposed at," "disposed near" and variations thereof are intended to mean that one element can be integral with another element, or that one element can be a separate structure bonded to or placed with or placed near another element.

(d) "Elastic," "elasticized" and "elasticity" mean that property of a material by virtue of which it tends to recover its original size and shape after removal of a force causing a deformation.

(e) "Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

(f) "Extension," "extend" and "extended" mean the change in length of a material due to stretching, expressed in units of length.

(g) "Fabrics" is used to refer to all of the woven, knitted and nonwoven fibrous webs.

(h) "Flexible" refers to materials which are compliant and which will readily conform to the general shape and contours of the wearer's body.

(i) "Force" includes a physical influence exerted by one body on another which produces acceleration of bodies that are free to move and deformation of bodies that are not free to move.

(j) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(k) "Integral" is used to refer to various portions of a single unitary element rather than separate structures bonded to or placed with or placed near one another.

(l) "Inward" and "outward" refer to positions relative to the center of an absorbent garment, and particularly transversely and/or longitudinally closer to or away from the longitudinal and transverse center of the absorbent garment.

(m) "Layer" when used in the singular can have the dual meaning of a single element or a plurality of elements.

(n) "Liquid communication" means that liquid such as urine is able to travel from one layer to another.

(o) "Liquid lmpermeable" when used to describe a layer or laminate means that liquid such as urine will not pass through the layer or laminate under ordinary use conditions in a direction generally perpendicular to the plane of the layer or laminate at the point of liquid contact.

(p) "Member" when used in the singular can have the dual meaning of a single element or a plurality of elements.

(q) "Nonwoven web" means a web of material which is formed without the aid of a textile weaving or knitting process.

(r) "Operatively joinedo and operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(s) "Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

(t) "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

(u) "Unadhered" refers to an absence of bonds of sufficient strength to withstand the forces typically encountered during ordinary wearing of the article.

These terms may be defined with additional language in the remaining portion of the specification.

DETAILED DESCRIPTION OF THE PREFERRED EMBODIMENTS

With reference to FIGS. 1–4, an absorbent article formed according to the invention is shown for purposes of illustration as a disposable undergarment 20 for adult incontinence. The invention may also be embodied in other types of absorbent articles, such as other adult care products, reusable absorbent articles, disposable diapers, training pants, feminine hygiene products, other personal care or health care garments, or the like.

In general, the undergarment 20 includes a garment shell 45 and a plurality of containment beams 50. Each containment beam 50 is bonded along an attachment edge 62 to an interior surface 46 of the garment shell 45 so that the containment beam is pivotable about and axis defined by the attachment edge in response to lateral compression of the garment shell, extension or contraction of elastic members, absorption of liquids, or a combination of these factors. The containment beams 50 are desirably the principle means by which the undergarment 20 retains liquids.

To facilitate the undergarment 20 having a bucket shape, the containment beams 50 are transversely spaced from the longitudinal center line 22 of the garment shell 45 and located near leg elastic members 48. Further, a relatively flexible material 51 for acquiring and/or distributing liquid is desirably located between the containment beams 50. To promote comfort, the containment beams 50 desirably have a width to thickness ratio of at least about 3:1, and more particularly at least about 5:1. In particular embodiments, pairs of containment beams 50 are provided in a shingled arrangement, and further, the absorbent structures 52 within the containment beams may be in a shingled arrangement as well. Absorbent articles employing containment beams 50 have been tested and found to have a beneficial impact on reducing leakage compared to present commercial undergarments.

Figure 2:
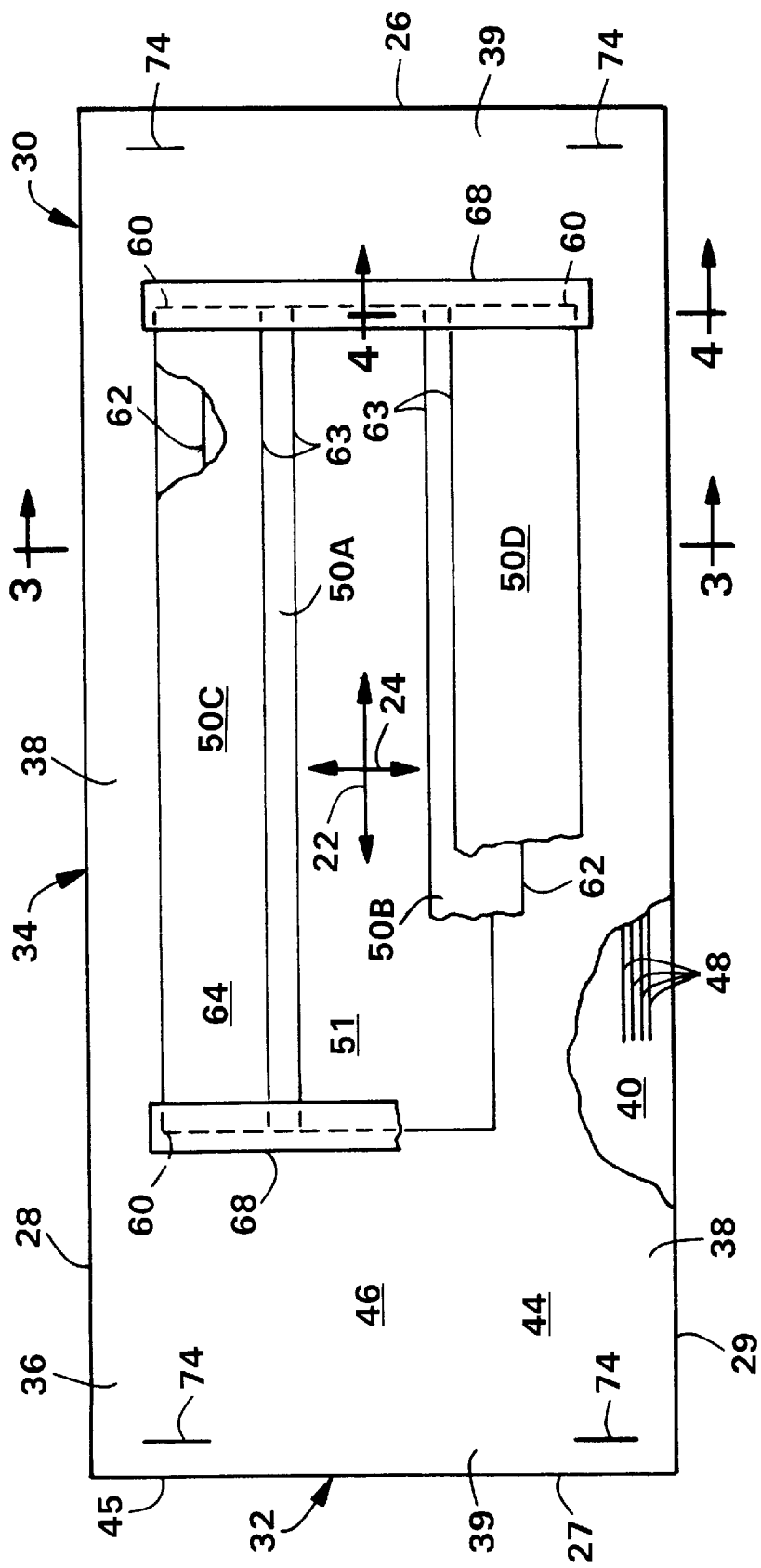
FIG. 2 representatively shows a plan view of portions of the disposable absorbent article shown in FIG. 1, taken from the bodyside of the absorbent article in a stretched and laid flat condition and with portions broken away for purposes of illustration.

The illustrated undergarment 20 defines a longitudinal axis or center line and a transverse axis or centerline, represented by arrows 22 and 24 in FIG. 2. The undergarment 20 has opposite, front and back longitudinal end edges 26 and 27, and first and second longitudinal side edges 28 and 29 that extend between the longitudinal end edges. The undergarment 20 includes a first or front waist region 30, a second or back waist region 32, and an intermediate, crotch region 34 positioned between and interconnecting the front and back waist regions. The outer edges of the undergarment 20 define a periphery 36 in which the longitudinally extending side margins are designated 38 and the laterally extending end margins are designated 39. The end edges 26 and 27 and side edges 28 and 29 are shown as generally straight, but optionally, may be curvilinear and contoured.

The front waist region 30 is contiguous with the front end edge 26 and extends longitudinally inward therefrom toward the transverse center line 24 of the undergarment 20. The back waist region 32 is contiguous with the back end edge 27 and extends longitudinally inward therefrom toward the transverse center line. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer. Thus, the crotch region 34 is the area where insults of urine typically occur in the undergarment or other disposable absorbent article.

The illustrated undergarment 20 includes a substantially liquid impermeable moisture barrier 40 and a substantially liquid permeable bodyside liner 44. The moisture barrier 40 and bodyside liner 44 are bonded together, such as by ultrasonic bonds, thermal bonds, adhesives, or other suitable means. The peripheries of the moisture barrier 40 and the bodyside liner 44 form the side and end margins 38 and 39 of the undergarment 20. Conventional absorbent products typically employ some form of absorbent structure between the layers functioning as the moisture barrier and the bodyside liner. In the present undergarment 20, however, the liquid containment beams 50 minimize or eliminate the need for such an absorbent structure. Nevertheless, in particular embodiments of the present invention, it may be desirable to include a tissue layer or a thin layer of cellulose fibers between the moisture barrier 40 and bodyside liner 44 in areas where there are no containment beams 50.

The moisture barrier 40 desirably comprises a material that is formed or treated to be liquid impermeable. Alternatively, the moisture barrier 40 may comprise a liquid permeable material and other suitable means (not shown) may be provided to impede liquid movement away from the crotch region 34 and the liquid containment beams 50. The moisture barrier 40 may also be vapor permeable, such that vapors encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides.

The bodyside liner 44 provides a soft, nonirritating surface against the skin of the wearer. Accordingly, a separate layer functioning as a bodyside liner may not be needed if the moisture barrier 40 is sufficiently soft and nonirritating to be positioned against the skin. If used, the bodyside liner 44 may be formed of either a liquid permeable material or, if no layers functioning as absorbent or liquid handling layers are disposed beneath the body liner, a liquid impermeable material. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably nonelastic and may be treated with a surfactant to aid in liquid transfer. In a particular embodiment of the invention, the bodyside liner 44 comprises a nonwoven, spunbond polypropylene fabric composed of about 2.8 to 3.2 denier fibers formed into a web having a basis weight of about 22 gram per square meter (gsm) and density of about 0.06 gm/cc. The fabric is surface treated with about 0.28 weight percent of a surfactant commercially available from Union Carbide Chemicals and Plastics Company, Inc. of Danbury, Conn., U.S.A., under the trade designation Triton X-102.

The portions of the undergarment 20 including the moisture barrier 40, bodyside liner 44 if used, and components therebetween, will be referred to as a garment shell and will be designated reference numeral 45. The garment shell 45, shown in a stretched and laid flat condition in FIG. 2, is illustrated as having a rectangular periphery 36. Of course, the garment shell 45 may optionally be hourglass-shaped, I-shaped, T-shaped, or irregularly-shaped. The garment shell 45 has an interior surface 46 which is intended to face the wearer when the undergarment 20 is worn, and an opposite exterior surface 47. In the illustrated embodiment, the interior surface 46 is generally provided by the bodyside liner 44 and the exterior surface 47 is generally provided by the moisture barrier 40.

Desirably although not necessarily, the garment shell 45 also includes leg elastic members 48 to draw and hold the side margins 38 of the undergarment 20 against the legs of the wearer and form a seal therewith. The elongated leg elastic members 48 are longitudinally orientated in each side margin 38, extending toward the front and back end edges 26 and 27. The leg elastic members 48 are positioned in the illustrated embodiment between the moisture barrier 40 and the bodyside liner 44. Using ultrasonic bonds, adhesives, thermal bonds, or other suitable means, the leg elastic members 48 are operatively joined in a stretched condition to the moisture barrier 40, the bodyside liner 44, or both, in either a straight or a curved shape. Alternatively, the leg elastic members 48 may be operatively joined in a relaxed state to a gathered portion of the moisture barrier 40, the bodyside liner 44, or both.

The leg elastic members 48 may be formed of a dry-spun coalesced multifilament elastomeric thread sold under the tradename LYCRA® and available from E.I. Du Pont de Nemours and Company. Alternately, the elastic members 48 may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. No. 4,938,754 to Mesek and U.S. Pat. No. 4,388,075 to Mesek et al.

In one aspect of the invention, the liquid retention capacity of the undergarment 20 is principally provided by a number of liquid containment beams 50. The undergarment 20 shown in FIGS. 1–4 includes four containment beams 50, although the particular number of containment beams may vary. For ease of reference, the containment beams 50 will be referred to individually as a first inner containment beam 50A, a second inner containment beam 50B, a first outer containment beam 50C, and a second outer containment beam 50D. The undergarment 20 also desirably includes material, referred to as an acquisition/distribution material 51, that is positioned between the inner containment beams 50A and 50B and adapted to initially take in liquids quickly and/or transport the liquids to the containment beams 50. The acquisition/distribution material 51 is adapted by capillary attraction, hydrophilic properties, or other suitable means to take in and then release the liquid to the containment beams 50.

Figure 3:
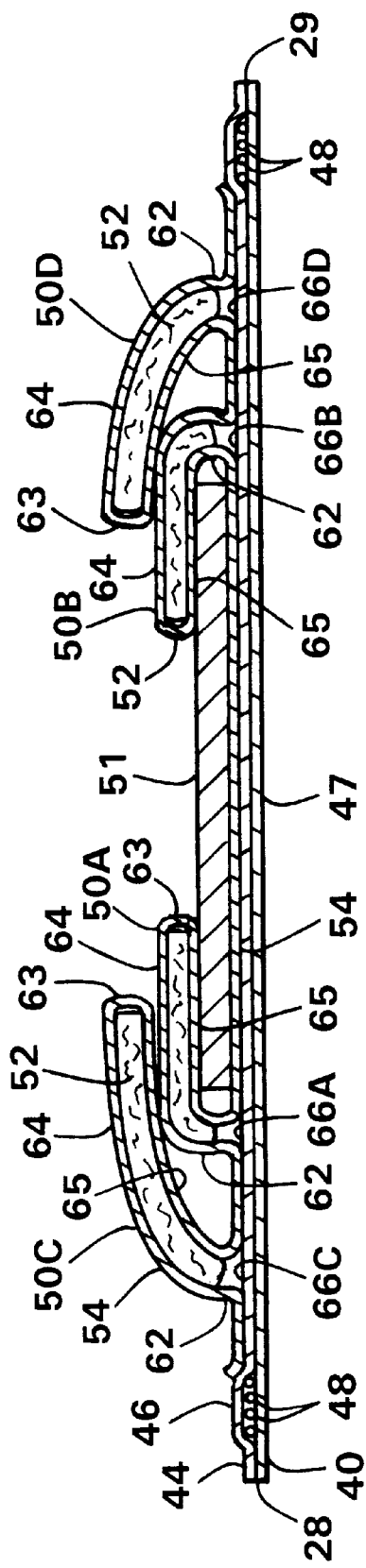
FIG. 3 representatively shows an enlarged section view taken generally from the plane of the line 3—3 in FIG. 2.
Figure 4:
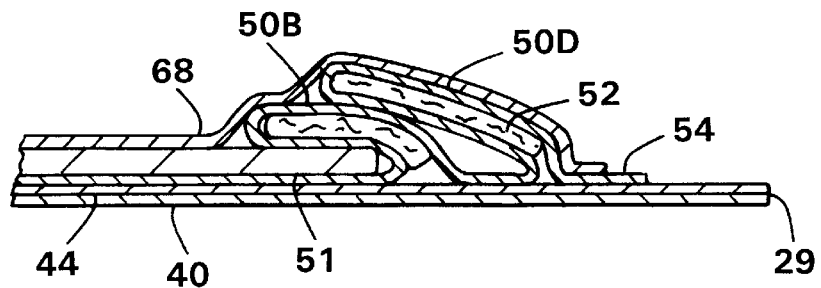
FIG. 4 representatively shows an enlarged section view taken generally from the plane of the line 4—4 in FIG. 2.

Each of the illustrated containment beams 50 is desirably non-elastomeric and comprised of an absorbent structure 52 positioned within a portion of a support layer 54 FIGS. 3 and 4. The absorbent structures 52 comprise materials adapted to absorb and retain liquid waste. The absorbent structures 52 may comprise various absorbent materials, such as an air-formed batt of cellulosic fibers (for example, wood pulp fluff), a coform material composed of a mixture of cellulosic fibers and synthetic polymer fibers, other air-laid composites, or the like. Polymer fibers may be incorporated, for example, in t he manner described in U.S. Pat. No. 5,227,107 issued Jul. 13, 1993, to Dickenson et al. The absorbent structures 52 may also comprise compounds such as organic or inorganic high-absorbency materials, which are typically capable of absorbing at least about 15 and desirably more than 25 times their weight in water. Suitable swellable high-absorbency materials are described in U.S. Pat. No. 4,699,823 issued Oct. 13, 1987, to Kellenberger et al. and U.S. Pat. No. 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Collods, Inc. The absorbent structures 52 may also include tissue layers or acquisition or distribution layers to help maintain the integrity of fibrous absorbents or transport liquids (not shown). The individual containment beams 50 may have identical absorbent structures 52 or absorbent structures that differ from one another in density, basis weight, materials, material amounts, or other such characteristics.

Figure 10:
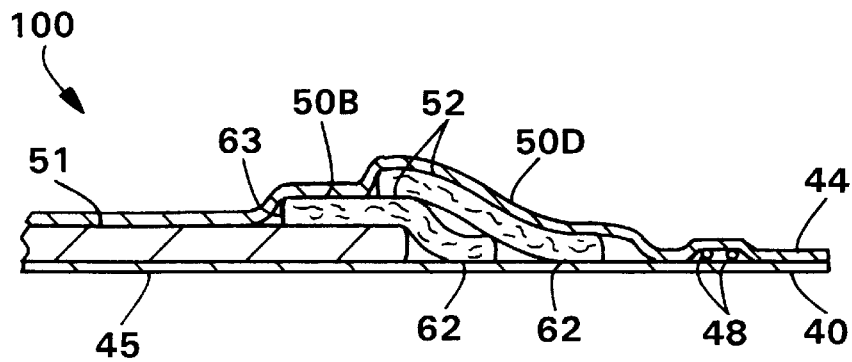
FIG. 10 representatively shows an enlarged section view similar to FIG. 8, but illustrating another alternative embodiment of the invention.

Each of the absorbent structures 52 is almost completely enclosed within a portion of the support layer 54. The support layer 54 functions to contain an absorbent structure 52 while also allowing liquids to pass through to the absorbent structure. The support layer 54 may also function to distribute liquids along and around the absorbent structures 52. The support layer 54 is bonded at spaced locations to the bodyside liner 44, thereby bonding each of the containment beams 50 to the interior surface 46 of the garment shell 45. As best shown in FIG. 3, the support layer 54 may comprise one integral layer extending across substantially the entire width of the garment shell 45, with different, transversely spaced portions wrapping each of the absorbent structures 52. The support layer 54 is bonded to the bodyside liner 44 adjacent one of the long edges of each absorbent structure 52. Alternatively, a separate support layer 54 may be provided for each absorbent structure 52 (not shown), or no support layer need be used (FIG. 10).

The support layer 54 is desirably formed of a liquid permeable material that is soft and does not irritate the skin of the wearer. The support layer 54 may comprise a woven, knit or nonwoven web. Suitable nonwoven webs include spunbonded, meltblown or bonded-carded webs composed of synthetic polymer filaments or fibers, such as polypropylene, polyethylene, polyesters or the like, or webs of natural polymer filaments or fibers such as rayon or cotton. The support layer 54 may also be treated with a surfactant to aid in liquid transfer to the absorbent structures 52. In particular embodiments, the support layer 54 comprises a single layer construction made from a 20.3 gsm (0.6 osy) thermally bonded web with 100 percent 3 denier polyethylene sheath and polyester core bicomponent staple fibers available from BASF Corporation of Enka, N.C., USA.

Each containment beam 50 is a generally planar structure having opposite longitudinal ends 60 which define therebetween a length dimension (FIG. 2). Each of the containment beams 50 also has an attachment edge 62 and an opposite free edge 63 which extend between the longitudinal ends 60 (FIGS. 2 and 3). A width dimension of each containment beam 50 is defined between the attachment and free edges 62 and 63. The width and length dimensions of each containment beam 50 dictate the size of opposite top and bottom surfaces 64 and 65 of each containment beam 50. The distance between the top and bottom surfaces 64 and 65 defines a thickness dimension of each containment beam 50.

The containment beams 50 are bonded to the garment shell 45 so that the containment beams are moveable in response to lateral compression of the garment shell, extension or contraction of the leg elastic members 48, absorption of liquids, or a combination of these factors. One particular method of bonding the containment beams 50 to the garment shell 45 is illustrated in detail in the transverse section view of FIG. 3. The attachment edge 62 of the first inner containment beam 50A is bonded to the interior surface 46. More particularly, the support layer 54 is wrapped around the absorbent structure 52 and bonded to the bodyside liner 44 at a bond region 66A. Adhesives, ultrasonic bonds, thermal bonds, mechanical bonds or other suitable means may used to bond the containment beams 50 to the interior surface 46. The location at which the containment beam 50A is attached to the interior surface 46 defines the attachment edge 62. As a result of this method of attachment and the shape of the containment beam 50A, the bottom surface 65 of the first inner containment beam 50A can lay down flat against the acquisition/distribution material 51. Desirably, the bottom surface 65 and the free edge 63 are unadhered to the acquisition/distribution material 51 so that the first inner containment beam 50A is adapted to move relative to the garment shell 45. More precisely, the containment beam 50A is adapted to pivot about an axis defined by its attachment edge 62. While the free edges 63 are illustrated as positioned closer to the longitudinal center line 22 than the attachment edges 62, it should be apparent that the orientation of the containment beams 50 could be reversed so that the free edges are transversely outward of the attachment edges when positioned flush against the interior surface 46.

The first outer containment beam 50C is attached in a similar manner, with the attachment edge 62 bonded to the interior surface 46 at a bond region 66C (FIG. 3). The bond region 66C for the first outer containment beam 50C is located between the bond region 66A for the first inner containment beam 50A and the first side edge 28. Attachment of the first outer containment beam 50C in this way allows the bottom surface 65 of the first outer containment beam 50C to lay down flat against the top surface 64 of the first inner containment beam 50A. The bottom surface 65 and the free edge 63 of the first outer containment beam 50C are desirably unadhered to the first inner containment beam 50A so that the first outer containment beam 50C is adapted to move relative to the garment shell 45, and in particular pivot about an axis defined by its attachment edge 62.

As suggested in FIG. 3, the second inner and outer containment beams 50B and 50D are bonded to the interior surface 46 of the garment shell 45 in a similar manner. The bond regions 66B and 66D where the attachment edges 62 of the second inner and outer containment beams 50B and 50D are bonded to the bodyside liner 44 lie between the longitudinal center line 22 and the second side edge 29. If desired, the support layer 54 may be bonded to the bodyside liner 44 and/or moisture barrier 40 transversely outward of bond regions 66C and 66D and between the bond regions 66. The inner containment beams 50A and 50B are considered to lie against the interior surface 46 if they are directly contacting the layer forming the interior surface, such as the bodyside liner 44, or if they are directly contacting a layer, such as acquisition/distribution layer 51, which is bonded to the layer forming the interior surface.

With reference to FIGS. 1, 2 and 4, end seals 68 may optionally be attached to the interior surface 46. The illustrated end seals 68 are bonded over the longitudinal ends 60 of the containment beams 50 to maintain the bottom surfaces 65 of the inner containment beams 50A and 50B at the longitudinal ends 60 against the interior surface 46 and to maintain the bottom surfaces 65 of the outer containment beams 50C and 50D at the longitudinal ends 60 against the inner containment beams 50A and 50B. The end seals 68 may be formed of any woven or nonwoven material, either liquid permeable or liquid impermeable, and which is desirably soft and not irritating against the skin of the wearer. As discussed in relation to the embodiment of FIG. 11, the end seals 68 may be liquid impermeable and function to limit longitudinal migration of liquid. The end seals 68 may be bonded to the interior surface 46 using adhesives, ultrasonic bonds, thermal bonds, mechanical bonds, or other suitable means.

The spacing between the free edges 63 of the inner containment beams 50A and 50B is a function of the width of the containment beams 50A and 50B and location of their bond regions 66A and 66B. The distance between the free edges 63 of the inner containment beams 50A and 50B, measured when the undergarment 20 is in a stretched and laid flat condition and the containment beams are directed inward against the interior surface 46, is desirably from 0 to about 10 centimeters (cm), and more desirably from about 0 to about 4 cm. Alternatively, the distance between the free edges 63 may be greater for larger products. Still alternatively, the free edges 63 of the inner containment beams 50A and 50B may touch or overlap one another (not shown). The containment beams 50 may be attached so that they are parallel, curved or perpendicular to the longitudinal axis 22 of the undergarment 20.

In one aspect of the invention, the shape of the containment beams 50 is selected to enhance comfort when the undergarment 20 is worn. Because the containment beams 50 are desirably attached to the interior surface 46 at a substantial relative distance from the longitudinal center line 22, it has been recognized that the containment beams 50 should desirably possess a ratio of the width dimension to the thickness dimension of at least about 3:1, so as not to be uncomfortable, particularly when the wearer is sitting. More desirably, the ratio of the width dimension to the thickness dimension is at least about 5:1, and particularly from about 8:1 to about 10:1, for enhanced comfort. In a particular embodiment, the containment beams 50 have a maximum width dimension of about 2 cm and a maximum thickness dimension of about 0.4 cm, resulting in a width to thickness ratio of 5:1. The length of the containment beams 50 is suitably from about 25 to 100 percent of the length of the undergarment 20. The width of the containment beams 50 may be constant over the length of the containment beams as illustrated, or alternatively the width may vary, such as by becoming wider toward each longitudinal end 60 (not shown).

In another aspect of the invention, the pivotable containment beams 50 are positioned in a shingled arrangement to further improve comfort. The outer containment beams 50C and 50D are adapted to lay against the top surfaces 64 of the inner containment beams 50A and 50B, respectively. Further, the attachment edges 62 of the outer containment beams 50C and 50D are desirably spaced from the attachment edges 62 of the inner containment beams 50A and 50B by from 0 to about 100 percent of the width of the outer containment beams 50C and 50D. More particularly, the attachment edges 62 of the outer containment beams 50C and 50D are spaced from the attachment edges of the inner containment beams 50A and 50B by from about 25 to about 60 percent of the width of the outer containment beams. This shingled arrangement of the containment beams 50 provides a gradual increase and then decrease in thickness of the undergarment 20 in the transverse direction, for improved comfort.

The acquisition/distribution material 51 helps to decelerate and diffuse surges of liquid that may be introduced into the crotch region 34 of the garment shell 45. In the illustrated embodiment, for example, the acquisition/distribution material 51 is located on and bonded directly to the portion of the support layer 54 that is located between the inner containment beams, which in turn is located on and bonded directly to the interior surface 46 of the garment shell 45. Alternatively, the acquisition/distribution material 51 may be interposed between the support layer 54 and the bodyside liner 44 or interposed between bodyside liner 44 and moisture barrier 40.

The acquisition/distribution material 51 may comprise any woven or nonwoven web adapted to quickly take in and/or transport liquids. For example, the acquisition/distribution material 51 may comprise a nonwoven web such as a spunbonded, meltblown or bonded-carded web composed of synthetic polymer filaments or fibers, such as polypropylene, polyethylene, polyesters or the like, or a web of natural polymer filaments or fibers such as rayon or cotton. The acquisition/distribution material may comprise a nonwoven fibrous web composed of a substantially hydrophobic material. In one particular embodiment, the acquisition/distribution material comprises a 100 gsm (3.0 osy) web formed of a homogeneous blend of 60 percent 3 denier polyethylene/polypropylene fibers available under the trade designation ESC-HR5 from Chisso Corporation of Osaka, Japan and 40 percent 6 denier polyester fibers available under the trade designation T-295 from Hoechst Celanese Corporation of Sommerville, N.J., USA, and bonded at 129 degrees Celsius (265 degrees Fahrenheit) for 1.8 seconds. Other suitable configurations of the acquisition/distribution material 51 are described in U.S. Pat. No. 5,192,606 issued Mar. 9, 1993, to D. Proxmire et al.; U.S. Pat. No. 4,798,603 issued Jan. 17, 1989, to S. Meyer et al.; U.S. Pat. No. 5,364,382 issued Nov. 15, 1994, to M. Latimer et al.; U.S. patent application Ser. No. 757,760 of W. Hanson et al. filed Sep. 11, 1991 (Attorney docket No. 9922); U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference.

The attachment system in the illustrated embodiment includes a pair of strap members 70 and fastening components to releasably attach the strap members to the front and back waist regions 30 and 32. The fastening components include a retainer 72 in the form of a button bonded at each end of each strap member 70. The retainers 72 may be releasably secured in slits 74 formed in the garment shell 45. When the undergarment 20 is positioned on the wearer, the straps 70 extend between the front and back slits 74 so that the retainers 72 may be releasably secured in the slits. This attachment system is described in U.S. Pat. No. 4,315,508 to Bolick, which is incorporated herein by reference. Optionally, other types of attachment systems, such as tapes, stretchable side panels, self-engaging geometric shaped materials, such as hooks, loops, bulbs, mushrooms, arrowheads, balls on stems, or the like, may be employed.

The strap members 70 (FIG. 1) are each generally rectangular strips of material, which is desirably an elastic material capable of stretching to approximately 2.8 to 3 times its relaxed length. The strap members 70 desirably have a length from about 15 to about 41 centimeters (cm.), and a width from about 1 to about 5 cm. For example, each strap member 70 may be 28 cm. long and 2.5 cm. wide. The cut ends of the strap members 70 may be bonded by ultrasonics, adhesives or other suitable means to prevent raveling.

Figure 5:
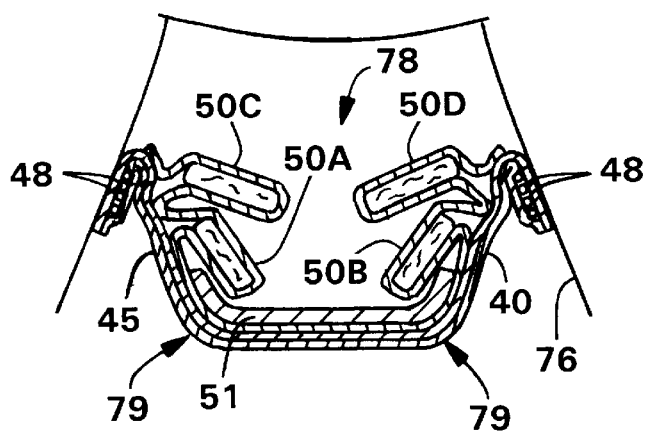
FIG. 5 representatively shows a transverse section view of the absorbent article of FIG. 1 while positioned to simulate the article being worn.

In use, the undergarment 20 is positioned on the body of the wearer and secured in position using the attachment system. A transverse section view of the undergarment 20 against a contoured surface 76, which represents the legs of a wearer, is shown in FIG. 5 to simulate the position of the undergarment during use. The interaction of the strap members 70 (FIG. 1) and the leg elastic members 48 cause the side margins 38 to be drawn against the legs of the wearer. It should also be noted that lateral compression of the undergarment 20 between the legs and extension of the leg elastic members 48 may cause the containment beams 50 to pivot away from the interior surface 46 of the garment shell 45.

The garment shell 45 defines an acquisition zone 78 (FIGS. 1, 5 and 6) which is the region of the garment shell that is likely to directly receive insults of liquid. For purposes of the present invention, the acquisition zone 78 shall be considered to consist of the central one-third of the garment shell 45 in the longitudinal direction 22 and the central one-third of the garment shell in the transverse direction 24, measured while the garment shell is in a stretched and laid flat position. In the illustrated embodiment, the acquisition/distribution material 51 covers the interior surface 46 of the garment shell 45 in the acquisition zone 78.

In one aspect of the invention, the undergarment 20 tends to form a bucket shape (FIG. 5) with the containment beams 50 located along the sidewalls of the bucket and forming an inwardly-extending lip of the bucket. The acquisition/distribution material 51 in the acquisition zone 78 forms the bottom of the bucket. The containment beams 50 are desirably located in the transverse direction 24 between the acquisition zone 78 and the first and second side edges 28 and 29. More particularly, the attachment edges 62 of the containment beams 50 are desirably bonded to the interior surface 46 at a transverse location outward of the acquisition zone 78 and at or inward of the position of the leg elastic members 48. Specifically, the attachment edges 62 of the containment beams 50 are desirably located between 0 to about 5 cm from the leg elastic members 48, and more desirably between 0 to about 2.5 cm for improved performance. By positioning the containment beams 50 in the outer transverse thirds of the garment shell 45, the containment beams tend to form part of the sidewalls of the bucket shape. Additionally, the acquisition zone 78 is desirably more flexible than the outer transverse thirds of the garment shell 45. As a result of the greater flexibility of the acquisition zone 78 and the use of separate, independent containment beams 50, the garment shell 45 tends to form inflection points 79 between the inner containment beams 50A and 50B. The containment beams 50 are located transversely outward of the inflection points 79 forming the sidewalls of the bucket shape, and the acquisition zone 78 is located between the inflection points forming the bottom of the bucket shape.

Figure 6:
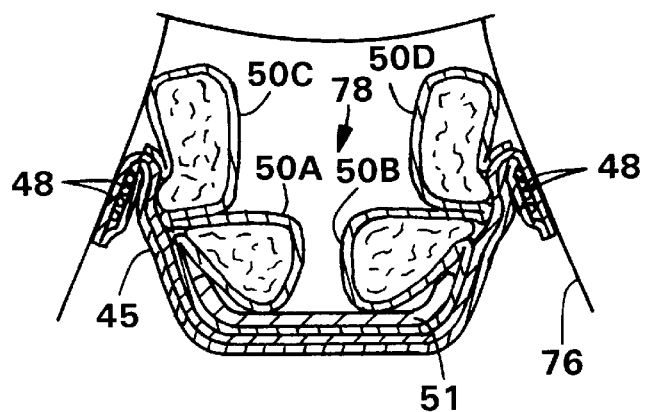
FIG. 6 representatively shows a section view similar to FIG. 5, although illustrating the absorbent article after liquid has been absorbed.

In another aspect of the invention, the acquisition zone 78 (FIGS. 5 and 6) of the undergarment 20 provides void space to rapidly take in multiple insults of liquid. FIG. 6 shows a transverse section view of the undergarment 20 similar to FIG. 5, but illustrating the position of the containment beams 50 after the undergarment has absorbed an insult of liquid. Insults of liquid tend to be quickly taken up by the acqulsition/distribution material 51 and subsequently desorbed by the absorbent structures 52 of the containment beams 50. Consequently, the containment beams 50 may tend to swell as illustrated in FIG. 6. The acquisition zone 78 and the region between the containment beams 50 continue to provide void space to accept additional insults of liquid. Further, the partially or fully swollen containment beams 50 tend to function at least in part as physical barriers to lateral liquid flow.

The undergarment 20 may be constructed so that the acquisition zone 78 has a saturated liquid retention capacity that is from 0 to about 50 percent, such as from 0 to about 30 percent, of the total saturated liquid retention capacity of the undergarment. More desirably, to maintain the void volume of the acquisition zone 78, the undergarment 20 is constructed so that the acquisition zone comprises less than about 10 percent, and even more desirably less than about 5 percent, of the total saturated retention capacity of the undergarment. By way of illustration, an acquisition zone 78 in an undergarment 20 adapted for use by moderately incontinent adults may have a saturated retention capacity of from about 30 to about 50 grams.

The saturated retention capacity of the acquisition zone 78 and the remaining portions of the undergarment can be determined by cutting the acquisition zone from the undergarment, measuring the saturated retention capacity of both, and comparing the value obtained for just the acquisition zone to the total value of the acquisition zone and the remaining portions. It should be understood that the free edges 63 of the containment beams 50 may be positioned over the acquisition zone 78 but do not form part of the acquisition zone if the attachment edges 62 are bonded to the interior surface 46 transversely outward from the acquisition zone. The saturated retention capacity of the acquisition zone 78 and the remaining portions of the undergarment can be determined according to the Saturated Retention Capacity Test as set forth in the TEST PROCEDURES section below. In particular embodiments, the undergarment 20 is constructed so that the containment beams 50 comprise from about 50 to 100 percent of the saturated liquid retention capacity of the undergarment, and more particularly from about 90 to 100 percent for improved performance.

Figure 7:
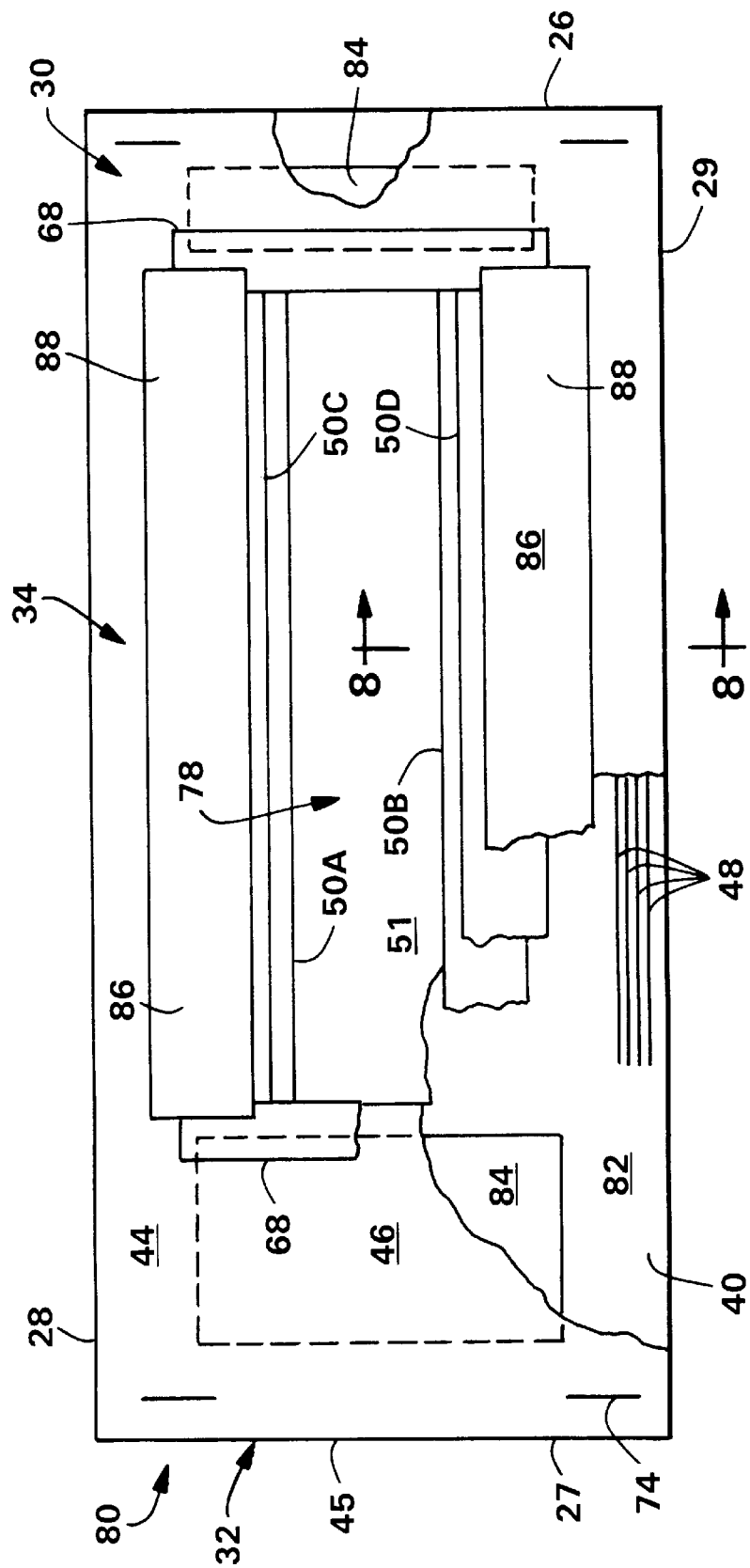
FIG. 7 representatively shows a plan view of portions of an alternative absorbent article according to the invention, taken from the bodyside of the absorbent article in a stretched and laid flat condition and with portions broken away for purposes of illustration.
Figure 8:
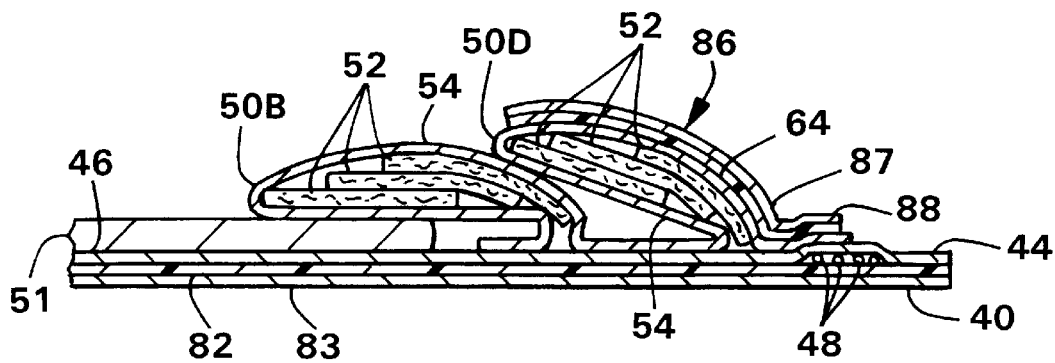
FIG. 8 representatively shows an enlarged section view taken generally from the plane of the line 8—8 in FIG. 7.

An alternative undergarment 80 according to the present invention is illustrated in FIGS. 7 and 8, where components similar to those previously described have been given the same reference numeral. The undergarment 80 includes first and second inner liquid containment beams 50A and 50B and first and second outer liquid containment beams 50C and 50D, all bonded to the interior surface 46 of a garment shell 45. An acquisition/distribution material 51 is positioned between the inner liquid containment beams 50A and 50B, and longitudinal end seals 68 may be provided to tack down the longitudinal ends 60 of the containment beams 50.

The garment shell 45 includes a bodyside liner 44 and a moisture barrier 40, the latter of which may comprise a liquid impermeable inner layer 82 and a soft outer layer 83. In one particular embodiment, the inner layer 82 comprises a cast or blown film formed of polypropylene, polyethylene or the like, and the outer layer 83 comprises a spunbond web formed of polypropylene and polyethylene medium-crimped bicomponent fibers in a 50/50 side-by-side configuration. The inner and outer layers 82 and 83 may be bonded together such as by a patterned application of adhesive, by thermal bonds, or other suitable means.

The garment shell 45 of the undergarment 80 also includes optional supplemental absorbent assemblies 84 disposed between the bodyside liner 44 and the moisture barrier 40. The supplemental absorbent assemblies 84 are desirably positioned between the acquisition zone 78 and the front and back end edges 26 and 27 of the garment shell 45 to improve fit, comfort and liquid absorbency in the front and back waist regions 30 and 32. Alternatively, the supplemental absorbent assemblies 84 may also be disposed in the crotch region 34 of the undergarment 80. The supplemental absorbent assemblies 84 may be formed of layers of tissue, wood pulp fluff, or other absorbent materials such as those described above in relation to the absorbent structures 52 of the containment beams 50. Elastic members such as leg elastic members 48 are also desirably bonded between the bodyside liner 44 and the moisture barrier 40. To enhance the ability of the elastic members 48 to shape the undergarment 20, the supplemental absorbent assemblies 84 are desirably not attached directly to, and therefore uncoupled from, the containment beams 50.

As best illustrated in FIG. 8, each of the containment beams 50 includes a plurality of individual absorbent structures 52 within a support layer 54. The individual absorbent structures 52 within each containment beam 50 are in a shingled arrangement, wherein the individual absorbent structures are positioned on top of one another but also offset from one another in the transverse direction 24. This shingled arrangement of the absorbent structures 52 within each of the containment beams 50, as well as the shingled arrangement of the outer containment beams 50C and 50D over the inner containment beams 50A and 50B, provides a gradual increase and then decrease in thickness of the undergarment 80 in the transverse direction 24, for improved comfort. The illustrated containment beams 50 include three individual absorbent structures 52 per containment beam, although the particular number may vary. Alternatively, a single absorbent structure 52 having a gradually increasing and then decreasing thickness profile in the transverse direction 24 may be used (not shown).

The undergarment 80 also includes leakage barriers 86 that are bonded to the top surface 64 of the outer containment beams 50C and 50D to inhibit lateral migration of liquids and present a dry surface against the legs of the wearer. The leakage barriers 86 may be formed of any soft, liquid impermeable material. For example, the leakage barriers may comprise a two layer adhesive composite consisting of a liquid impermeable layer 87 and a soft nonwoven layer 88. In one embodiment, the leakage barriers 86 comprise an adhesive laminate of a 17 gsm (0.5 osy) 2.5 denier spunbond polypropylene and a 0.01 millimeter polyolefin based film. As shown in FIG. 8, portions of the leakage barriers 86 may extend transversely outward of the outer containment beams 50C and 50D and be bonded to the interior surface 46, inward of the side edges 28 and 29. The leakage barriers 86 may be bonded to the containment beams 50 and the interior surface 46 using adhesives, ultrasonic bonds, thermal bonds, mechanical bonds, or other suitable means.

Figure 9:
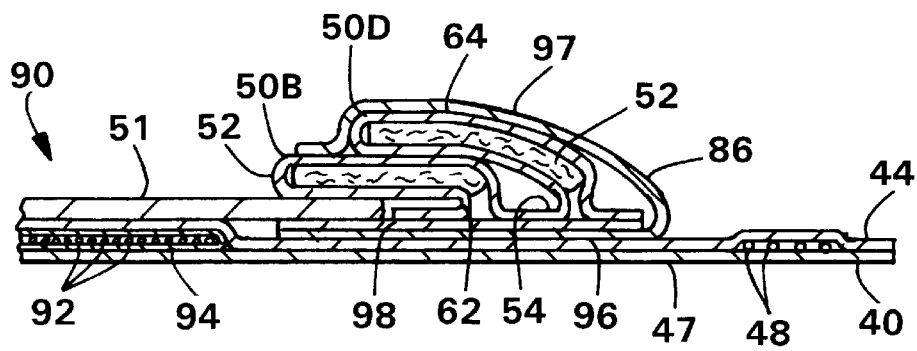
FIG. 9 representatively shows an enlarged section view similar to FIG. 8, but illustrating an alternative embodiment of the invention.

A further alternative construction of an undergarment 90 according to the present invention is partially illustrated in FIG. 9. The undergarment 90 includes a bodyside liner 44 bonded to a moisture barrier 40, with leg elastic members 48 positioned therebetween. The moisture barrier 40 desirably comprises a vapor permeable and substantially liquid impermeable material. Alternatively, the moisture barrier 40 may comprise several regions with at least one region being vapor permeable and substantially liquid impermeable.

The moisture barrier 40 suitably comprises, for example, a material having a water vapor transmission rate (WVTR) value of at least about 100 grams per square meter per 24 hours ($gm/m^2/24$ hr). More particularly, the moisture barrier 40 comprises a material having a WVTR value of at least about 2,000 $gm/m^2/24$ hr, and more desirably having a WVTR of at least about 3,000 $gm/m^2/24$ hr, for improved performance. One suitable procedure for measuring the WVTR value of a material is set forth in the TEST PROCEDURES section below. The moisture barrier 40 may comprise, for example, any micro-porous,"breathable" material which permits gases, such as water vapor, to escape while substantially preventing liquid exudates from passing therethrough. Suitable breathable materials include a microporous polymer film or a nonwoven fabric which has been coated or otherwise treated to impart a desired level of liquid impermeability, or the like. For example, a suitable microporous film is available under the trade designation PMP-1 from Mitsui Toatsu Chemicals, Inc., a company having offices in Tokyo, Japan; or a polyolefin film available under the trade designation XKO-8044 from 3M Company of Minneapolis, Minn., USA.

The undergarment 90 also includes desiccant particles 92 positioned between the moisture barrier 40 and the bodyside liner 44. The desiccant particles 92 minimize the formation of condensation which may tend to form on the exterior surface 47 of the breathable moisture barrier 40. The desiccant particles 92 may be wrapped in an envelope 94 comprising, for example, a nonwoven web such as a tissue or spunbond material. Alternatively or in addition thereto, the desiccant particles 92 may be held in place with adhesives or other components (not shown). The undergarment 90 also includes an acquisition/distribution material 51, and the desiccant particles may alternatively be positioned between the bodyside liner 44 and the acquisition/distribution material. Desiccant particles 92 suitable for use in the undergarment 90 include calcium chloride, calcium oxide, superabsorbent materials, silica gel, or the like. In one embodiment, an envelope 94 is formed by two layers measuring 10.16 by 40.64 centimeters which are bonded together and 1.0 gram of calcium oxide (CaO) is evenly distributed between the layers. Each layer comprises a 13.5 gsm (0.4 osy) point bonded web formed of 50 percent polyethylene sheath/50 percent polypropylene core 2.6 denier bicomponent fibers.

To further minimize the potential formation of condensation on the outer surface of the breathable moisture barrier 40, the undergarment 90 is provided with leakage barriers 86 at least partially positioned between the containment beams 50 and the moisture barrier. The leakage barriers 86 will thus tend to isolate the absorbent structures 52 of the containment beams 50 from the moisture. barrier 40, as well as inhibiting lateral migration of liquids and providing a dry surface against the legs of the wearer. The leakage barriers 86 desirably have a base portion 96 bonded to the moisture barrier 40 and an exposed portion 97 bonded to the top surface of at least the outer containment beams 50C and 50D. As illustrated, the exposed portion 97 extends inward a sufficient distance so that it is positioned against and bonded to at least a portion of the top surface 64 of each inner containment beam 50A and 50B as well.

The undergarment 90 may optionally be provided with a distribution layer 98 to promote liquid movement from the acquisition/distribution material 51 to the containment beams 50. The distribution layer 98 is desirably bonded onto the base portion 96 of the leakage barriers 86 using adhesives, ultrasonic bonds, thermal bonds, mechanical bonds or other suitable means. The distribution layer 98 is positioned on top of the base portion 96 so that it is in liquid communication with the containment beams 50. The attachment edges 62 of the containment beams 50 are then bonded to the distribution layer 98. Most desirably, the inner portion of the distribution layer 98 overlaps the outer portion of the acquisition/distribution material 51 so that the distribution layer and acquisition/distribution material are in liquid communication.

The distribution layer 98 may comprise any material that directs liquid flow in one or more directions in the plane defined by the length and width of the distribution layer. The distribution layer 98 is suitably a nonwoven web made of cellulosic fibers or thermoplastic fibers, such as polyethylene, polypropylene, polyester, or the like, and can be formed as a bonded carded web, a meltblown web, a spunbonded web, or blends thereof. In one specific embodiment, the distribution layer 98 comprises a 75 gsm (2.2 osy) hydroentangled pulp sheet made with soft wood pulp available from Kimberly-Clark Corporation of Neenah, Wis., U.S.A. under the trade designation Longlac 19. The pulp sheet includes 1 weight percent surfactant available from Witco Chemical Corporation, Organics Division, of Melrose, Ill., USA under the trade designation AROSURF® PA727. The distribution layer 98 may alternatively comprise slivers, sliver-like materials, sulfonated pulps, or the like.

Another alternative construction of an undergarment 100 according to the present invention is partially illustrated in FIG. 10. The undergarment 100 includes a bodyside liner 44bonded to a moisture barrier 40, with containment beams 50 , acquisition/distribution material 51, and leg elastic members 48 all disposed between the bodyside liner and the moisture barrier. The bodyside liner 44is desirably bonded directly to the moisture barrier 40 and acquisition/distribution material 51, but need not be bonded directly to the containment beams 50 to allow for movement of the containment beams.

The containment beams 50 of the undergarment 100 consist of absorbent structures 52 and do not include support layers 54 as illustrated in the previous embodiments. The absorbent structures 52 desirably have sufficient integrity to be bonded along their attachment edges 62 to the moisture barrier 40 and to remain an integral structure even after absorbing liquid. For example, the absorbent structures may comprise a coform material formed of a matrix of thermoplastic polymer fibers and individualized wood pulp fibers disposed throughout the matrix. Suitable coform materials are disclosed in U.S. Pat. No. 4,100,324 issued Jul. 11, 1978, to Anderson et al.; U.S. Pat. No. 4,604,313 issued Aug. 5, 1986, to McFarland et al.; and U.S. Pat. No. 5,350,624 issued Sep. 27, 1994, to Georger et al.; the disclosures of which are incorporated herein by reference. Particularly where the containment beams 50 are bonded to the moisture barrier 40 in the manner illustrated in FIG. 10, it will be apparent that a portion of the absorbent structure 52 remote from the free edge 63 may optionally not be bonded directly to the moisture barrier 40, provided the containment beam has a portion functioning as an attachment edge and the free edge is moveable relative to the garment shell 45. Because the bodyside liner 44 is positioned over the containment beams 50, the liner is not considered to form part of the garment shell 45 in this embodiment.

Figure 11:
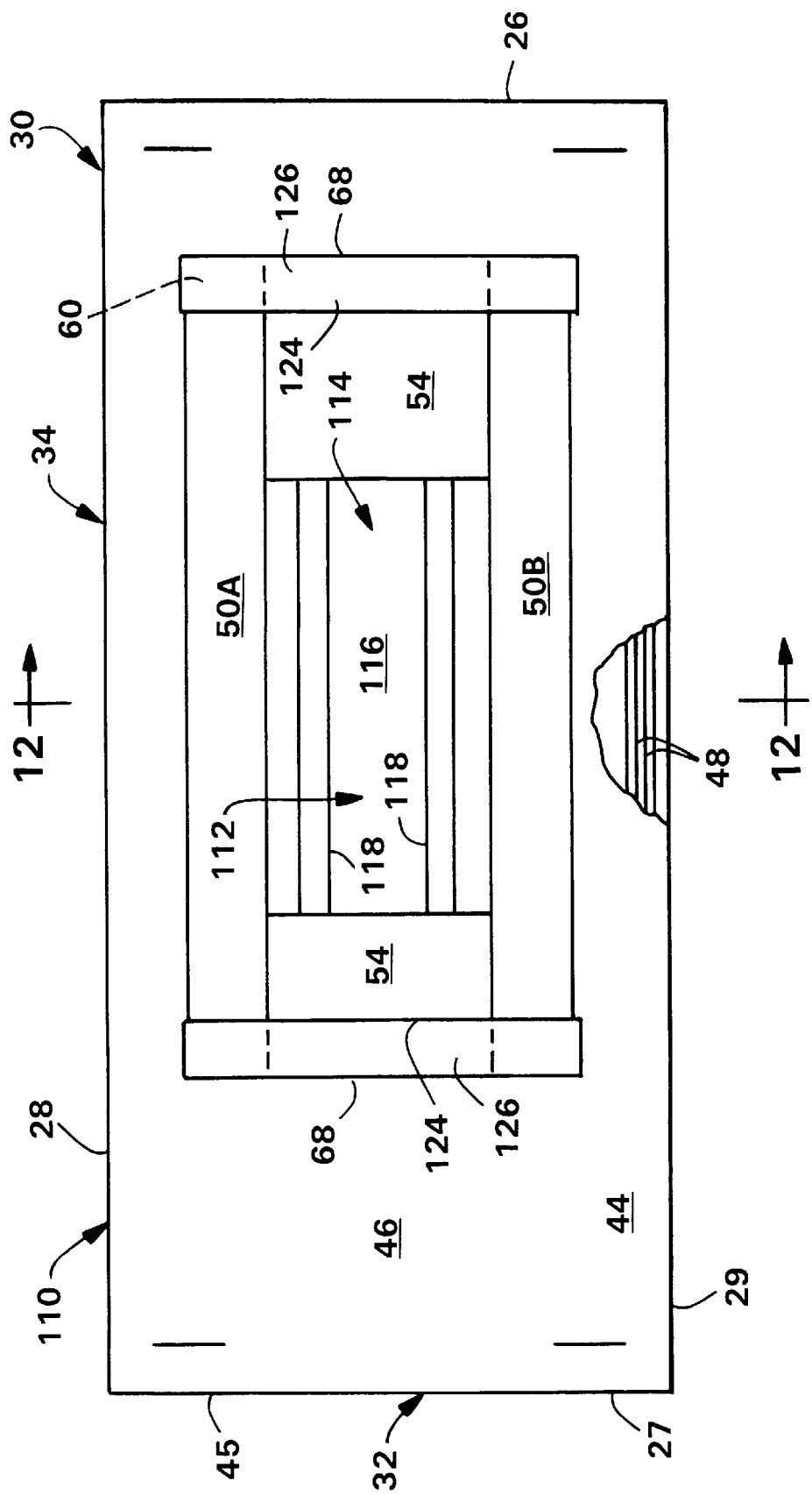
FIG. 11 representatively shows a plan view of portions of a further alternative absorbent article according to the invention, taken from the bodyside of the absorbent article in a stretched and laid flat condition and with portions broken away for purposes of illustration.
Figure 12:
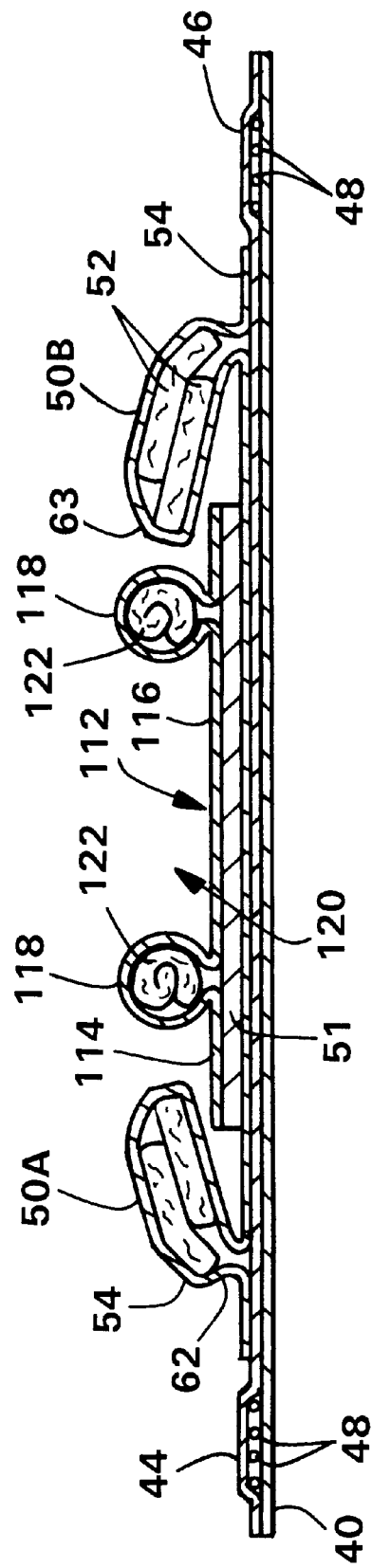
FIG. 12 representatively shows an enlarged section view taken generally from the plane of the line 12—12 in FIG. 11.

A still further alternative undergarment 110 according to the present invention is illustrated in FIGS. 11 and 12. The undergarment 110 includes a garment shell 45 with a bodyside liner 44 bonded to a moisture barrier 40, and leg elastic members 48 positioned therebetween. First and second containment beams 50A and 50B are bonded to the interior surface 46 of the garment shell 45, with an acquisition/distribution assembly 112 positioned between the containment beams. The acquisition/distribution assembly 112 comprises an inner acquisition/distribution material 51 and an outer acquisition/distribution liner 114.

The acquisition/distribution liner 114 includes a facing layer 116 that is folded and bonded to itself to form a pair of peaks 118 that are separated by a channel 120 (FIG. 12). The facing layer 116 may be formed of a wide variety of liquid permeable materials, including but not limited to woven materials such as cloth, knit materials, permeable films, foams and fibrous nonwoven materials. In one particular embodiment, the facing layer 116 comprises a single layer construction made from a 20.3 gsm (0.6 osy) thermally bonded carded web material utilizing 100 percent 3 denier bicomponent staple fibers from BASF Corporation. The fibers are 38 millimeters (mm) (1.5 in) in length and comprise a polyethylene sheath surrounding a polyester core. One suitable acquisition/distribution material 51 comprises a single layer structure, such as a 20.3 gsm (0.6 osy) through-air bonded carded web made completely from 1.8 denier polyethylene sheath/polypropylene core bicomponent fibers having a length of 38 mm (1.5 in) and available from BASF Corporation.

A filler 122 formed of a resilient, liquid permeable material is folded upon itself and disposed within the peaks 118. In one embodiment, the filler 122 comprises strips of a 85 gsm (2.5 osy) bonded carded web including 60 weight percent 3 denier polyethylene sheath/polyester core bicomponent staple fibers available from BASF Corporation under the trade designation CS-2 and 40 weight percent 6 denier rayon fibers available from Courtaulds Fibers, Inc. of Axis, Ala., USA. Facing layers 116 of the foregoing type are disclosed in U.S. patent application Ser. No. 169,449 by M. Weber et al., filed Dec. 17, 1993, and titled "Liquid Absorbent Material For Personal Care Absorbent Articles And The Like"(Attorney Docket No. 10,880), the disclosure of which is incorporated herein by reference.

The containment beams 50A and 50B of the undergarment 110 each comprise a pair of absorbent structures 52 wrapped in a common support layer 54. The absorbent structures 52 are somewhat offset in the transverse direction 24 so as to be in a shingled relationship.

The undergarment 110 also includes end seals 68 to maintain the longitudinal ends 60 of the containment beams 50 against the interior surface 46 of the garment shell 45 and to provide a physical barrier to longitudinal movement of liquid. In this particular embodiment, the end seals 68 are formed of an elastomeric material and have integral first and second portions 124 and 126 adjacent the opposite longitudinal edges of the end seal. The first portions 124 are positioned closer to the transverse center line 24 of the undergarment 110 and are desirably unadhered to the interior surface 46. In contrast, the second portions 126 are positioned further from the transverse center line 24 and are directly bonded to the interior surface 46. In this way, the first portions 124 tend to stand up from the interior surface 46 and form longitudinal liquid barriers when the end seals 68 are allowed to contract. The end seals 68 desirably do not substantially gather the garment shell 45 in the transverse direction 24.

Containment beams 50 as described in relation to the foregoing embodiments may also be employed on other disposable absorbent products. Examples of such products, for instance, are disclosed in U.S. patent application Ser. No. 08/168,615 by T. Roessler et al., filed Dec. 16, 1993, and titled "Dynamic Fitting Diapers"(Attorney Docket No. 10,961); U.S. patent application Ser. No. 08/168,615 by E. D. Johnson et al., filed Aug. 12, 1994, and titled "Diaper With Improved Lateral Elongation Characteristics" (Attorney Docket No. 11,629); and U.S. Pat. No. 4,940,464 issued Jul. 10, 1990, to P. Van Gompel et al.

The following EXAMPLES are provided to give a more detailed understanding of the invention. The particular amounts, proportions, compositions and parameters are meant to be exemplary, and are not intended to specifically limit the scope of the invention.

TEST EXAMPLE 1

A number of test undergarments representing one embodiment of the present invention were constructed. These test undergarments included a moisture barrier formed of a polyethylene film and measuring 68.6 by 22.1 cm. Leg elastic members were operatively joined to the moisture barrier along the two side margins in the crotch region of the garment.

The test undergarments included two containment beams each measuring 54.6 cm long, 3.2 cm wide, and 1 cm thick. Each containment beam included three identical absorbent structures stacked on top of one another. The absorbent structures were formed of a mixture of 50 weight percent wood pulp fluff and 50 weight percent superabsorbent particles. The absorbent structures were substantially fully wrapped in a single support layer formed of a 20 gsm thermally bonded carded web of polyethylene sheath and polyester core bicomponent fibers from BASF Corporation, which were treated with 1.5 weight percent surfactant available from Union Carbide Chemicals and Plastics Company, Inc. under the trade designation Triton X-102. The support layer was bonded to the moisture barrier so that each containment beam was pivotable about an axis defined by its attachment edge. The containment beams were curved slightly so that the free edges of the containment beams were spaced apart by about 4 cm at their longitudinal center and spaced apart by about 7 cm at their longitudinal ends. The containment beams were generally centered in the longitudinal direction of the undergarment and spaced from the leg elastic members by about 2.5 cm. The two containment beams had a combined saturated retention capacity of about 450 rams.

An acquisition/distribution assembly was positioned between the containment beams and bonded to the support layer. The acquisition/distribution assembly comprised an acquisition/distribution material disposed on and bonded to the support layer between the containment beams. The acquisition/distribution material measured 54.6 cm long and 10.2 cm wide and comprised a 50 gsm spunbond web formed of side-by-side polypropylene/polyethylene bicomponent fibers.

The acquisition/distribution assembly also included an acquisition/distribution liner similar to that illustrated in FIGS. 11 and 12. The acquisition/distribution liner measured 25.4 by 10.2 cm and was bonded onto the acquisition/distribution material. The acquisition/distribution liner included a facing layer that was folded and bonded to itself to form a pair of peaks that were separated by a channel. A filler was positioned in the peaks, and the facing layer was bonded to a backing layer.

The facing and backing layers each comprised of a single layer construction made from a 20.3 gsm thermally bonded carded web material utilizing 100 percent 3 denier bicomponent staple fibers from BASF Corporation. The fibers, which were 38 mm in length and comprised a polyethylene sheath surrounding a polyester core, were treated with 1.5 weight percent surfactant available from Union Carbide Chemicals and Plastics Company, Inc. under the trade designation Triton X-102. The filler comprised strips of an 85 gsm bonded carded web including 60 weight percent 3 denier polyethylene sheath/polyester core bicomponent staple fibers available from BASF Corporation under the trade designation CS-2 and 40 weight percent 6 denier rayon fibers available from Courtaulds Fibers, Inc. of Axis, Ala., USA.

The acquisition/distribution assembly also included two relatively narrow strips of acquisition/distribution material disposed between the acquisition/distribution liner and the 54.6 by 10.2 cm layer of acquisition/distribution material. The strips, which were stacked on top of one another, measured 25.4 by 2.5 cm and 25.4 by 5.1 cm. The strips were formed of the same material as the 54.6 by 10.2 cm layer of acquisition/distribution material.

The acquisition zone of the undergarment, defined as the central one third of the garment shell in the longitudinal direction and the central one third of the garment shell in the transverse direction, comprised less than 5 percent of the total saturated retention capacity of the undergarment.

The test undergarments also included a single peak structure positioned between each containment beam and each set of the leg elastic members. Each peak structure was identical in construction and materials as the peaks formed in the acquisition/distribution liner. The peak structures outward of the containment beams, however, were 35.6 cm long, whereas the peaks of the acquisition/distribution liner were only 25.4 cm long.

End seals formed of a liquid impermeable material and measuring 2.5 by 15.2 cm were positioned over the longitudinal ends of the containment beams and bonded to the support layer. Additionally, a bodyside liner material was bonded to the moisture barrier in locations not covered by the support layer. The bodyside liner comprised a 20 gsm spunbond web formed of polypropylene fibers.

The fastening system for the test undergarments included two strap members that were formed of an elastic material purchased from Shelby Elastics of Shelby, N.C., USA. The strap members had a length of about 26 cm and a width of about 2.5 cm. Buttons were attached near each end of each strap member, and reinforced buttonholes were formed on each undergarment.

COMPARATIVE EXAMPLE 1

The undergarments of Test Example 1 were evaluated relative to comparative undergarments corresponding to undergarments of the type sold in about August of 1994 by Kimberly-Clark Corporation under the tradename Depend®. The comparative undergarments included a moisture barrier, leg elastic members, and a fastening system similar to those used in the test undergarments.

A generally planar absorbent assembly was disposed on the moisture barrier. The absorbent assembly measured 59.4 by 14.5 cm and was formed of cellulose fluff, sprayed polypropylene filaments, and superabsorbent particles. The absorbent assembly was wrapped in tissue and the tissue was attached to the moisture barrier using a construction adhesive. A bodyside liner was disposed on the absorbent assembly and bonded to the moisture barrier outward of the absorbent assembly. The bodyside liner comprised a 20 gsm spunbond polypropylene web that was treated with 1.5 weight percent surfactant available from Union Carbide Chemicals and Plastics Company, Inc. under the trade designation Triton X-102. The comparative undergarments had a saturated retention capacity of about 450 grams.

For purposes of analyzing the performance of the undergarments of Test Example 1, a forced failure test was conducted. The test used 36 participants including 18 men and 18 women. The participants were each fitted with an apparatus that included a flexible tube having an exit end positioned in the crotch region. Each participant was asked to wear either the Test Example 1 undergarment or the Comparative Example 1 undergarment, selected randomly, under an appropriately sized pair of underwear. After the participant wore the undergarment for 30 minutes, the participant was seated and the undergarment was then loaded through the tube with three insults of 24 milliliters (ml) of 0.9 percent saline solution spaced 60 seconds apart. Two minutes later, the participant rose to a standing position while a gush of 72 ml of saline solution was infused into the tube. The participant remained standing for two minutes after which time the participant was seated. Additional insults of 24 ml of saline solution were loaded through the tube at 60 second intervals until leakage occurred. This procedure was repeated so that each participant tested each of the Test Example 1 undergarments and each of the Comparative Example 1 undergarments twice.

The undergarments of Test Example 1 were found to have absorbed an average of about 186.85 grams of liquid at the point of leakage compared to an average of about 146.49 grams of liquid at the point of leakage for the undergarments of Comparative Example 1. Table 1 below shows the average loading value at the point of leakage for each participant for the two Test Example 1 undergarments and the two Comparative Example 1 undergarments. The average and standard deviation values were calculated from the individual observed values rather than the mean values shown in the table.

TABLE 1

| Participant | COMPARATIVE EXAMPLE 1 | | TEST EXAMPLE 1 | |
|---|---|---|---|---|
| | Mean | Std Dev | Mean | Std Dev |
| 1 | 107.50 | 20.51 | 195.50 | 20.51 |
| 2 | 164.50 | 3.54 | 175.50 | 9.19 |
| 3 | 127.00 | 18.38 | 127.50 | 43.13 |
| 4 | 117.50 | 28.99 | 117.00 | 28.28 |
| 5 | 94.00 | 2.83 | 95.00 | 1.41 |
| 6 | 118.00 | 4.24 | 184.00 | 36.77 |
| 7 | 134.50 | 48.79 | 202.00 | 16.97 |
| 8 | 191.50 | 30.41 | 181.50 | 17.68 |
| 9 | 177.00 | 14.14 | 179.50 | 50.20 |
| 10 | 121.50 | 0.71 | 178.50 | 16.26 |
| 11 | 134.00 | 49.50 | 215.50 | 31.82 |
| 12 | 177.00 | 15.56 | 227.50 | 14.85 |
| 13 | 131.50 | 16.26 | 156.50 | 14.85 |
| 14 | 109.50 | 14.85 | 253.50 | 45.96 |
| 15 | 103.50 | 17.68 | 249.00 | 46.67 |
| 16 | 224.00 | 8.49 | 250.50 | 13.44 |
| 17 | 212.00 | 28.28 | 195.00 | 70.71 |
| 18 | 181.50 | 21.92 | 279.00 | 57.98 |
| 19 | 131.00 | 21.21 | 226.50 | 14.85 |
| 20 | 143.50 | 4.95 | 217.00 | 39.60 |
| 21 | 141.50 | 64.35 | 283.00 | 35.36 |
| 22 | 168.00 | 1.41 | 262.00 | 36.77 |
| 23 | 164.00 | 25.46 | 167.50 | 4.95 |
| 24 | 203.00 | 14.14 | 266.00 | 36.77 |
| 25 | 112.00 | 33.94 | 121.50 | 34.65 |
| 26 | 119.00 | 103.24 | 191.50 | 106.77 |
| 27 | 176.50 | 20.51 | 164.00 | 25.46 |
| 28 | 215.50 | 4.95 | 137.50 | 68.59 |
| 29 | 165.50 | 4.95 | 238.50 | 3.54 |
| 30 | 190.00 | 7.07 | 192.00 | 5.66 |
| 31 | 117.50 | 41.72 | 136.00 | 73.54 |
| 32 | 121.50 | 28.99 | 176.50 | 113.84 |
| 33 | 120.00 | 2.83 | 167.50 | 2.12 |
| 34 | 137.50 | 53.03 | 129.00 | 41.01 |
| 35 | 117.50 | 31.82 | 97.00 | 0.00 |
| 36 | 104.00 | 18.38 | 91.00 | 4.24 |
| Average | 146.49 | 42.02 | 186.85 | 61.07 |

TEST EXAMPLE 2

A number of test undergarments having the general configuration of the undergarment 110 shown in FIGS. 11–12 were also constructed. The undergarments of Test Example 2 included a bodyside liner, end seals, leg elastic members, and a fastening system similar to those used in the undergarments of Test Example 1. The undergarments of Test Example 2 did not include the single peak structures between the containment beams and leg elastic members as were used in the undergarments of Test Example 1.

The undergarments of Test Example 2 included a moisture barrier comprised of an adhesive laminate of an inner layer and an outer layer. The inner layer comprised a liquid and vapor impermeable polyethylene film, and the outer layer comprised a point bonded spunbond nonwoven formed of polypropylene and polyethylene medium-crimped bicomponent fibers in a 50/50 side-by-side configuration. The moisture barrier measured 68.6 by 22.1 cm.

The undergarments of Test Example 2 included two containment beams each measuring 44.5 cm long, 3.2 cm wide, and 1 cm thick. Each containment beam included two identical absorbent structures slightly offset in the transverse direction so as to be in a shingled configuration (see FIG. 12). The absorbent structures were formed of a mixture of 80 weight percent wood pulp fluff and 20 weight percent superabsorbent particles. The absorbent structures were substantially fully wrapped in a single support layer formed of a 20 gsm thermally bonded carded web of polyethylene sheath and polyester core bicomponent fibers from BASF Corporation, which were treated with 1.5 weight percent surfactant available from Union Carbide Chemicals and Plastics Company, Inc. under the trade designation Triton X-102. The support layer was bonded to the moisture barrier so that each containment beam was pivotable about an axis defined by its attachment edge. The containment beams were curved slightly so that the distance between the free edges varied between about 5 and about 7 cm. The containment beams were skewed toward the front end edge of the undergarment and spaced from the leg elastic members by about 2.5 cm. The two containment beams had a combined saturated retention capacity of about 260 grams.

An acquisition/distribution assembly measuring 25.4 by 10.2 cm was positioned between the containment beams and bonded to the support layer. The acquisition/distribution assembly comprised an acquisition/distribution liner similar to that employed in the undergarments of Test Example 1. The acquisition/distribution liner measured 25.4 by 10.2 cm and was positioned between the containment beams and bonded to the support layer. The acquisition/distribution liner included a facing layer that was folded and bonded to itself to form a pair of peaks that were separated by a channel. A filler was positioned in the peaks, and the facing layer was bonded to a backing layer. The materials used to form the facing and backing layers and the filler were the same as in the undergarments of Test Example 1.

The acquisition/distribution assembly also included two relatively narrow strips of acquisition/distribution material disposed between the acquisition/distribution liner and the support layer. The strips, which were stacked on top of one another, measured 25.4 by 2.5 cm and 25.4 by 5.1 cm. The strips comprised a 50 gsm spunbond web formed of side-by-side polypropylene/polyethylene bicomponent fibers.

The acquisition zone of the undergarment, defined as the central one third of the garment shell in the longitudinal direction and the central one third of the garment shell in the transverse direction, comprised less than 5 percent of the total saturated retention capacity of the undergarment.

COMPARATIVE EXAMPLE 2

Comparative undergarments similar to those of Comparative Example 1 were also provided for purposes of evaluation. The undergarments of Comparative Example 2, however, were modified as follows. First, the tissue did not completely wrap the absorbent assembly so that a middle portion of one surface of the absorbent assembly was directly bonded to the moisture barrier using a construction adhesive. Second, the bodyside liner was directly bonded to the tissue using a construction adhesive. And third, the undergarments of Comparative Example 2 included an acquisition/distribution material measuring 25.4 by 10.2 cm. The acquisition/distribution material, which comprised a 75 gsm bonded carded web formed of polyethylene fibers, was bonded to the side of the bodyside liner facing the moisture barrier using a construction adhesive.

The performance of the undergarments of Test Example 2 and the undergarments of Comparative Example 2 was compared in a forced failure evaluation. This forced failure evaluation utilized 36 participants including 18 men and 18 women. The participants were each fitted with an apparatus that included a flexible tube having an exit end positioned in the crotch region. Each participant was asked to wear either the Test Example 2 undergarment or the Comparative Example 2 undergarment, selected randomly, under an appropriately sized pair of underwear. The undergarment was then loaded through the tube with an initial load of 100 ml of 0.9 percent saline solution while the participant was standing. After 30 minutes of wear time and in increments of 5 minutes thereafter, subsequent loads of 24 ml of saline solution were loaded through the tube while the participant was sitting, until leakage occurred. This procedure was repeated so that each participant tested each of the Test Example 2 undergarments and each of the Comparative Example 2 undergarments twice.

The undergarments of Test Example 2 were found to have absorbed an average of about 390.50 grams of liquid at the point of leakage compared to an average of about 151.88 grams of liquid at the point of leakage for the undergarments of Comparative Example 2. Table 2 below shows the average loading value at the point of leakage for each participant of the two Test Example 2 undergarments and the two Comparative Example 2 undergarments. The average and standard deviation values were calculated from the individual observed values rather than the mean values shown in the table. Participants 13, 17, 22, 30 and 35 only tested one of the Test Example 2 undergarments.

TABLE 2

| | COMPARATIVE EXAMPLE 2 | | TEST EXAMPLE 2 | |
|---|---|---|---|---|
| Participant | Mean | Std Dev | Mean | Std Dev |
| 1 | 127.00 | 2.83 | 442.50 | 61.52 |
| 2 | 107.50 | 16.26 | 308.50 | 60.10 |
| 3 | 155.00 | 63.64 | 505.50 | 34.65 |
| 4 | 172.00 | 4.24 | 394.00 | 16.97 |
| 5 | 149.00 | 72.12 | 315.00 | 91.92 |
| 6 | 168.50 | 2.12 | 395.00 | 65.05 |
| 7 | 164.50 | 0.71 | 480.00 | 121.62 |
| 8 | 180.67 | 32.33 | 354.00 | 308.30 |
| 9 | 241.00 | 69.30 | 356.50 | 111.02 |
| 10 | 174.00 | 12.73 | 398.50 | 152.03 |
| 11 | 180.00 | 46.67 | 476.00 | 39.60 |
| 12 | 137.00 | 16.97 | 410.00 | 5.66 |
| 13 | 131.00 | 24.04 | 342.00 | — |
| 14 | 96.00 | 1.41 | 313.00 | 32.53 |
| 15 | 104.50 | 2.12 | 335.00 | 69.30 |
| 16 | 99.50 | 2.12 | 215.50 | 26.16 |
| 17 | 126.50 | 34.65 | 233.00 | — |
| 18 | 150.50 | 2.12 | 269.00 | 60.81 |
| 19 | 170.00 | 2.83 | 339.00 | 134.35 |
| 20 | 202.00 | 15.56 | 635.00 | 31.11 |
| 21 | 152.50 | 48.79 | 525.50 | 89.80 |
| 22 | 168.00 | 70.71 | 507.00 | — |
| 23 | 152.00 | 63.64 | 446.00 | 24.04 |
| 24 | 209.50 | 14.85 | 474.00 | — |
| 25 | 116.00 | 16.97 | 361.00 | 39.60 |
| 26 | 107.00 | 18.38 | 323.00 | 60.81 |
| 27 | 110.00 | 14.14 | 278.50 | 19.09 |
| 28 | 117.50 | 28.99 | 357.00 | 14.14 |
| 29 | 126.00 | 39.60 | 296.50 | 85.56 |
| 30 | 164.00 | 31.11 | 505.00 | — |
| 31 | 182.50 | 10.61 | 487.50 | 31.82 |
| 32 | 196.50 | 43.13 | 474.50 | 55.86 |
| 33 | 167.00 | 1.41 | 497.50 | 21.92 |
| 34 | 154.00 | 0.00 | 411.00 | 28.28 |
| 35 | 163.00 | 32.53 | 292.00 | — |
| 36 | 131.50 | 14.85 | 310.00 | 8.49 |
| Average | 151.88 | 41.03 | 390.50 | 110.29 |

Several participants noted that the undergarments of Test Example 2 were less bulky than the undergarments of Comparative Example 2. Additionally, several participants noted that the undergarments of Test Example 2 did not feel uncomfortable in either the dry or wet state. It is hypothesized that the undergarments of Test Example 2 had a greater average loading value at the point of leakage compared to the undergarments of Test Example 1 because the containment beams of Test Example 2 provided greater open spaces for liquid to reside.

TEST PROCEDURES

Saturated Retention Capacity

The saturated retention capacity of a material is measured as follows. The material to be tested, having a moisture content of less than about 7 weight percent, is weighed and submerged in an excess quantity of room temperature (about 23 degrees Celsius) synthetic urine. The material to be tested is allowed to remain submerged for 20 minutes. After 20 minutes, the material is removed from the urine and placed on a Teflon™ coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4$ $7H_2O$), 1.33 grams potassium sulphate ($K_2SO_4$), 1.24 grams tribasic sodium phosphate dodecahydrate ($Na_3PO_4$ $12H_2O$), 4.4 grams sodium chloride (NaCl), 3.16 grams potassium chloride (KCl), 8.56 grams of urea ($CO(NH_2)_2$), 0.1 grams Pluronic 10R8 surfactant (a nonionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

Water Vapor Transmission Rate

A suitable technique for determining the WVTR (water vapor transmission rate) value of a material is ASTM Standard E96-80. For the purposes of the present invention, circular samples measuring 3 inches in diameter are cut from the test material and a control material which is a piece of CELGUARD® 2500 film from Hoechst Celanese Corporation of Sommerville, N.J., USA. CELGUARD® 2500 is a 0.0025 cm thick microporous polypropylene film. Five samples are prepared for each material. The test dish is a No. 60-1 Vapometer pan distributed by Thwing-Albert Instrument Company, Philadelphia, Pa., U.S.A. One hundred milliliters of water are poured into each Vapometer pan, and each of the samples of the test material and control material are placed across the open tops of the individual pans. Do not apply stopcock grease unless sample contamination can be avoided. Screw-on flanges are tightened to form a seal along the edges of the pans, leaving the associated test material or control material exposed to the ambient atmosphere over a 6.5 cm diameter circle having an exposed area of about 33.17 square centimeters. The pans are placed in a forced air oven set at 32° C. (100° F.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill., U.S.A. Upon completion of the equilibration, the pans are removed from the oven, weighed and immediately returned to the oven. After 24 hours, the pans are removed from the oven and weighed again. The preliminary test WVTR value is calculated as follows:

Test WVJR=(grams weight loss over 24 hours)×315.5 ($g/m^2$/24 hours)

The relative humidity within the oven is not specifically controlled.

Under predetermined set conditions of 32° C. (100° F.) and ambient relative humidity, the WVTR for CELGUARD® 2500 has been determined to be 5000 $gm/m^2$/24 hours. Accordingly, the CELGUARD® 2500 is run as a control sample with each test, and the preliminary test values are corrected to the set conditions using the following equation:

WVTR=(Test WVTR/control WVTR)×5000 $gm/m^2$/24 hr.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article, comprising:
   a garment shell comprising a moisture barrier and defining an interior surface;
   first and second inner liquid containment beams comprising an absorbent material; and
   first and second outer liquid containment beams, each of the inner and outer liquid containment beams having:
   longitudinal ends;
   opposite attachment and free edges which extend between the longitudinal ends; and
   opposite top and bottom surfaces;
   wherein the liquid containment beams comprise from about 90 to 100 percent of the total saturated retention capacity of the absorbent article and the attachment edge of each of the inner and outer liquid containment beams is bonded to the interior surface, the bottom surface of each of the inner containment beams is adapted to lie against the interior surface, the bottom surface of each of the outer containment beams is adapted to lie against the top surface of one of the inner containment beams, and each of the liquid containment beams is adapted to pivot about an axis defined by its attachment edge and be moveable relative to the moisture barrier.

2. The absorbent article of claim 1, wherein the garment shell has a first waist region, a second waist region, and a crotch region positioned between and interconnecting the first and second waist regions, and the crotch region includes an acquisition zone having lateral boundaries inboard of the attachment edges of the first and second inner liquid containment beams.

3. The absorbent article of claim 1, wherein the attachment and free edges define therebetween a width dimension, the top and bottom surfaces define therebetween a thickness dimension, and a ratio of the width dimension to the thickness dimension is at least about 5:1.

4. The absorbent article of claim 1, wherein each of the containment beams comprises an absorbent structure disposed within a liquid permeable support layer.

5. The absorbent article of claim 4, wherein the support layer comprises one integral layer that is bonded at spaced locations to the interior surface, a plurality of containment beams being wrapped within the support layer.

6. The absorbent article of claim 1, further comprising end seal means for maintaining the longitudinal ends of the inner containment beams against the interior surface and the longitudinal ends of the outer containment beams against the inner containment beams.

7. The absorbent article of claim 6, wherein the end seal means comprises an elastic and liquid impermeable material bonded to the interior surface.

8. The absorbent article of claim 1, further comprising an acquisition/distribution material disposed on the interior surface between the containment beams.

9. The absorbent article of claim 8, wherein the absorbent article forms a bucket shape, the containment beams forming sidewalls of the bucket and the acquisition/distribution material forming a floor of the bucket.

* * * * *